United States Patent
Bukshpan (10) Patent No.: US 6,514,203 B2
(45) Date of Patent: Feb. 4, 2003

(54) METHOD FOR ULTRASONIC CORONARY THROMBOLYSIS

(75) Inventor: Shmuel Bukshpan, Ramat Hasharon (IL)

(73) Assignee: Sonata Technologies Ltd., Rehovot (IL)

( * ) Notice: Subject to any disclaimer, the term of this patent is extended or adjusted under 35 U.S.C. 154(b) by 0 days.

(21) Appl. No.: 09/780,511

(22) Filed: Feb. 12, 2001

(65) Prior Publication Data

US 2002/0138003 A1 Sep. 26, 2002

(51) Int. Cl.[7] .............................. A61B 8/00; A61B 17/22
(52) U.S. Cl. .............................. 600/439; 600/458; 601/2
(58) Field of Search ................................ 600/439, 463, 600/466–467, 471; 601/2–3

(56) References Cited

U.S. PATENT DOCUMENTS

| | | | | |
|---|---|---|---|---|
| 5,307,816 A | * | 5/1994 | Hashimoto et al. | |
| 5,524,620 A | * | 6/1996 | Rosenschein | 601/2 |
| 6,050,947 A | * | 4/2000 | Rhyne et al. | 600/447 |
| 6,080,107 A | * | 6/2000 | Poland | 600/458 |
| 6,113,570 A | * | 9/2000 | Siegel et al. | 601/2 |

* cited by examiner

*Primary Examiner*—Francis J. Jaworski
(74) *Attorney, Agent, or Firm*—AlphaPatent Associates Lt; Daniel J. Swirsky (57) ABSTRACT

A method and apparatus for achieving ultrasonic coronary thrombolysis. After intravenous injection of a thrombus-specific ultrasound contrast agent, an array of ultrasonic transducers arranged in a pad placed on the patient's chest transmits ultrasound signals into the patient, from a virtual source. Reflected signals are then analyzed to determine the ratio of the second (or hall) harmonic to first harmonic components in the signals. A high ratio indicates the presence of a thrombus in the field of interrogation Time-of-flight data for each of the receivers is used to calculate a spatial location of the thrombus, and a phased array ultrasonic transmission is then focused on the thrombus, so as to achieve sonoparation.

19 Claims, 7 Drawing Sheets

METHOD FOR ULTRASONIC CORONARY THROMBOLYSIS

FIELD OF THE INVENTION

The present invention relates in general to thrombolysis of coronary artery blood clots, and in particular to achieving rapid lysis of coronary thromboses by means of transthoracic unsound.

BACKGROUND OF THE INVENTION

It is known that coronary artery thrombosis is a leading cause of morbidity and mortality in the western world today. In this condition, a blood clot forms in a coronary artery, resulting in absent or inadequate blood flow to part of the heart muscle (myocardium). If adequate blood supply to the myocardium is not reestablished within minutes of onset of the thrombosis, the myocardiurn undergoes ischenmia (cell damage), and later infarction (cell death). Effective treatment of coronary thrombosis thus depends on achieving dissolution of the thrombus (thrombolysis) as soon as possible after the onset of symptoms, and this is most commonly achieved by intravenous adminiration of a thrombolytic agent, such as tissue plasminogen activator (tpA).

Once a coronary thrombosis has been diagnosed, early thrombolysis is initiated as soon as possible. Ideally, this is done by medical or paramedical personnel at the point at which they first encounter the patient. Thus an ambulance team may initiate early thrombolysis prior to transporting a patient to the hospital or hospital staff may initiate thrombolysis immediately upon arrival of a patient in the Emergency Room.

As the rapidity with which coronary blood flow is reestablished determines the long-term prognosis for the patient, there has been much interest in finding ways of augmenting or replacing standard early thrombolytic treatment protocols so as to achieve more rapid or more effective thrombolysis. For an early thrombolytic technique to be clinically useful, however, it is necessary that the technique be easily administered by the first medical personnel to encounter the patient (often an ambulance team or Emergency Room staff), at the point at which they first encounter the patient (often in the patient's home or in the hospital Emergency Room), over a short period of time.

It is known that application of ultrasound energy to organic tissue can result in disruption of the tissue, if the intensity of the ultrasound energy focused on the tissue is high enough Thus, ultrasonic lithotripsy has become a standard method for treating renal stones, whereby ultrasound energy focused on a renal stone causes the stone to disintegrate. Blood clots, too, have been shown to undergo thrombolysis when exposed to high intensity ultrasonic energy, and this technique has been successfully used to achieve thrombolysis both in-vitro and in-vivo.

Despite the proven efficacy of ultrasound as a method for achieving thrombolysis, clinical application of this modality in the early treatment of coronary artery thrombosis has been inhibited by the technical difficulties involved in delivering effective amounts of ultrasound energy to coronary arteries, which are both small in diameter (measuring only a few millimeters) and highly mobile (due to the constant contraction and relaxation of the myocardium in which the arteries lie). Due to the mobility and small size of coronary thrombi, it has not been possible, to date, to reliably focus transthoracic ultrasound energy on a coronary thrombosis, as the focal point changes from second to second with the beating of the heart.

Real time ultrasonic localization of blood clots has been reported by Unger et al (The Use of a Thrombus-Specific Ultrasound Contrast Agent to Detect Thrombus in Arteriovenous Fistulae Investigative Radiology; volume 35; number 1: 86–89), who showed that injection of a thrombus-specific ultrasound contrast agent facilitated the ultrasonic diagnosis of clots in AV fistulae. In Unger's report, large amounts of contrast agent adhered to static clots, thus enabling the increased echogenicity of the clots to be appreciated on ultrasound imaging. This technique, however, does not work for thromboses in the small, low flow, coronary arteries, in which only small amounts of contrast agent adhere to the thrombi. Rosenscheim et al (Ultrasound Image Guided Noninvasive Ultrasound Thrombolysis, Circulation 2000;102:238–245) have described a method for ultrasonic diagnosis of peripheral blood clots combined with immediate ultrasound thrombolysis of the detected clots. Their technique for thrombolysis, however, is slow (taking several minutes), thus precluding it's use in coronary thrombi which change location with the beating of the heart every few seconds.

It should be noted that both of the above described methods for ultrasonic diagnosis and localization of vascular thrombi employ standard ultrasonic imaging techniques, whereby the amplitudes of reflected ultrasound waves are analyzed so as to construct an image of the thrombus. In terms of standard ultrasound imaging techniques, therefore, only objects which produce reflected ultrasound signals of sufficiently high amplitude as to allow the signals to be individually detected by the receiving ultrasound crystal can be imaged.

To date, several techniques for achieving coronary ultrasound thrombolysis have been described:

1. Administration of the ultrasound by means of an intravascular ultrasound (IVUS) transducer. In this technique, a small ultrasound transducer located on the tip of a coronary artery catheter is advanced through the coronary circulation and positioned on the thrombus. Ultrasound energy is then administered directly onto the clot, allowing a sufficient intensity of ultrasound energy to be achieved in the thrombus as to cause disruption of the blood clot. As the catheter in the artery moves along with the pulsations of the myocardium, unnecessary exposure of surrounding tissue to damaging ultrasound energy is minimized. Several authors have reported. the clinical use of intravascular ultrasound to achieve coronary thrombolysis. IVUS, however, suffers from the deficiency that it entails cardiac catheterization in a catheterization laboratory. It is thus very invasive and time consuming, and cannot be performed within minutes of the onset of symptoms in a patient suffering from a coronary thrombosis.

2. Administration of ultrasound to the entire thorax (Siegel et al: Noninvasive. Transthoracic, Low-Frequency Ultrasound Augments Thrombolysis in a Canine Model of Acute Myocardial Infarction Circulation. 2000;101:2026). In this technique as coronary angiography or IVUS are not performed, the exact spatial location of the coronary thrombosis is not known, and the entire thorax is exposed to ultrasound energy. So as to achieve a sufficient intensity of ultrasound energy in the blood clot, very high levels of ultrasound energy have to be used. This technique suffers from the deficiency that the ultrasound energy is not focused on the thrombus. Healthy tissue is thereby exposed to damaging levels of ultrasound energy. In addition, as the amount of ultrasound energy actually reaching the thrombus is small, very long treatment times (up to ninety minutes) are required to achieve thrombolysis. This technique is thus impractical and dangerous for use in humans, and not clinically useful as a method of early coronary thrombolysis.

3. Augmentation of extrathoracically applied ultrasound energy by an intravenous ultrasound contrast agent. (Wu Y et al: Binding and lysing of blood clots using X-408. Invest Radiol 1998:33: 880–885). In this technique, an ultrasound contrast agent such as MRX408 is administered intravenously, prior to the application of ultrasound energy to the entire thorax. It is known that ultrasound contrast agents may enhance the absorption of specific frequencies of ultrasound energy by the tissue to which the contrast agent is adhered. Administration of a contrast agent that specifically adheres to thrombi therefore decreases the amount of ultrasound energy that has to be administered extrathoracically so as to achieve an effective intensity of ultrasound energy in the clot. Although this technique entails lower exposure of healthy tissue to ultrasound energy than the technique of Siegel described above, this technique still suffers from the deficiency that up to thirty minutes of low energy ultrasound application is required to achieve thrombolysis. Shorter application times (five minutes) require the administration of dangerously high levels of ultrasound energy (420 kPa). This technique is thus too time consuming to be clinically useful as a method of early coronary thrombolysis.

Current techniques for achieving ultrasound thrombolysis of coronary blood clots are thus either laborious (requiring the performance of formal cardiac catheterization in a laboratory), time consuming (requiring at least 30 minutes of ultrasound exposure) or dangerous (due to excessive exposure of healthy tissue to damaging, unfocused, ultrasound energy). Thus, despite the efficacy of ultrasound as a modality for achieving thrombolysis, no currently known technique of ultrasound administration is clinically useful in the early treatment of coronary thrombosis.

There is therefore a need for, and it would be highly advantageous to have, a method for achieving ultrasonic coronary thrombolysis, which is rapid, portable and safe.

SUMMARY OF THE INVENTION

The present invention provides a method and apparatus for achieving thrombolysis of coronary artery thromboses by means of ultrasound energy. In terms of the present invention, a thrombus-specific ultrasound contrast agent is injected intravenously in a patient suspected of having a coronary thrombosis. An array of ultrasound transducers positioned on the patient's chest then transmit ultrasound signals into the patient's thorax, and receive the reflected echoes. Frequency or other temporal characteristics of the received echoes are analyzed by a computer processor in real time, so as to instantly identify and spatially localize coronary artery thromboses. Immediately upon identification and localization of a thrombus, ultrasound signals of sufficient energy to cause thrombolysis are transmitted into the thorax by the transducers, focused on the identified spatial location of the thrombus. The novelty of the present invention lies in the utilization only of frequency or other temporal characteristics of ultrasonic signals reflected off of coronary thrombi (as opposed to amplitude characteristics, as are utilized in all standard ultrasound imaging modalities) to localize the thrombi. In particular, the specific frequency characteristic utilized is the ratio, in the received signal, between the second and first harmonics of the ultrasound signal, where the first harmonic is the central frequency in which most of the energy had been transmitted.

Due to the small size of coronary artery thromboses, the amplitude of echoes reflected of off such thromboses is small, making it difficult to differentiate such echoes from background noise and achieve reliable two-dimensional imaging of coronary thromboses, using standard imaging techniques, even in the presence of an ultrasound contrast agent bound to the thrombus.

In addition to being generated by contrast bubbles, it is well known in the art that second harmonic components in reflected signals are also generated by native tissue, even in the absence of contrast bubbles. This native harmonic component is a disturbing factor when it is desired to detect contrast bubbles by utilizing the second harmonic component of a reflected signal, as in the case when bubbles are adherent to a coronary thrombus. A second harmonic component is also parasitically present in transmitted signals. This component, too, is a disturbing factor when it is desired to detect contrast bubbles by utilizing the second harmonic component of a reflected signal. To achieve optimal detection of second harmonic components of bubble origin, therefore, it is desirable to eliminate all signals which may originate in the native tissue, or which may parasitically be present in the transmitted signal.

The second harmonic content in the transmitted signal can be significantly reduced by appropriate tailoring of the envelop of the pulse, utilizing the technique of "windowing", by which the transmitted signal is multiplied in time by a 'window' (e.g. a Gaussian function) so as to minimize second harmonics of the transmitted frequency, in a manner known also as apodization. The second harmonic component generated by the tissue can be significantly reduced by utilizing the technique of "tissue native harmonic imaging." This technique is presently used in modern ultrasonic systems to improve sensitivity, and utilizes the amplitude characteristics of the received second harmonic signals to achieve two-dimensional imaging of organs, and the thrombus within. However, as tissue non-linearity results in the generation of harmonics (in the reflected signal) originating from both native tissue and contrast bubbles, amplitude-based imaging of these signals may still be inadequate to differentiate a small thrombus from surrounding native tissue.

The present invention is based on the observation that contrast bubbles exhibit a type of non-linearity which is different to that exhibited by native tissue. Typical bubble non-linearity in ultrasound reflection results in the generation of a second harmonic component which is relatively greater than that generated by native tissue, while the first harmonic components caused by bubble and native tissue non-linearity are relatively similar. Thus the ratio between the second and first transmitted harmonics of reflected echoes is notably higher for signals reflected off of a thrombus-specific ultrasound contrast agent than for signals reflected off of native organic tissues. Detection of a high ratio between the second and first transmitted harmonics thus indicates the presence of a thrombus in the ultrasonic field of interrogation Determination of this ratio can be achieved instantaneously by a standard computer processor receiving data input from the transducer array, without the need for actual amplitude-based visualization of the tissue under interrogation. Furthermore, as the array is comprised of several transducers at different locations to each other on the thorax, the spatial source of the reflected signal having a high second to first harmonic ratio can be geometrically calculated by the processor. As the calculations required to achieve diagnosis and localization of a thrombus by his method can be performed automatically and instantaneously, and as thrombolysis by means of the same transducer array can be initiated automatically by the computer processor (before the coronary artery has had time to move because of myocardial contraction), the method of the present invention allows for the rapid diagnosis and ultrasonic thrombolysis of coronary artery thromboses.

According to the teachings of the present invention, therefore, there is provided a method for diagnosing a thrombus, including introducing an ultrasound contrast agent into a human body, transmitting an ultrasound signal into the human body at at least one transmission frequency, receiving an ultrasound signal from the human body, quantifying a first temporal characteristic and a second temporal characteristic of the received ultrasound signal, describing a relationship between the first and second temporal characteristics, and inferring a diagnosis of a thrombus from the described relationship. There is farther provided a method for localizing a thrombus in a human body, including introducing an ultrasound contrast agent into the human body, transmitting an ultrasound signal towards the thrombus at at least one transmission frequency, receiving, at a plurality of locations, a plurality of ultrasound signals reflected off of the thrombus, each of the received ultrasound signals having an increased ratio of a first temporal characteristic to a second temporal characteristic, quantifying a time-of-flight for each of the received ultrasound signals, and calculating a spatial location of the thrombus from the time-of-flight quantities. There is further provided a method for lysing a thrombus in a human body, including introducing an ultrasound contrast agent into the human body, transmitting an ultrasound signal towards the thrombus at at least one transmission frequency, receiving an ultrasound signal reflected off of the thrombus, the received ultrasound signal having a temporal characteristic, calculating a spatial location of the thrombus from the temporal characteristic, and transmitting ultrasound energy towards the spatial location There is further provided an apparatus for treating a thrombus in a human body, including a sheet of material, the sheet being placeable on the human body, a plurality of ultrasound transmitters for transmitting ultrasound signals into the human body, the transmitters being fixedly located within the sheet, and the transmitters being oriented within the sheet such that the transmission is effected into the human body, a plurality of ultrasound receivers for receiving ultrasound signals reflected from the human body, the receivers being fixedly located within the sheet, and the receivers being oriented within the sheet such that the reception is effected from the human body, a layer of ultrasound coupling medium applied to a surface of the ultrasound transmitters and the ultrasound receivers, the layer being conformable to a contour of the human body, and a processor for processing the received signals, the processor being functional to calculate a temporal characteristic of the received signals, and diagnose a thrombus from the calculated temporal characteristic.

BRIEF DESCRIPTION OF THE DRAWINGS

The invention is herein described, by way of example only, with reference to the accompanying drawings, wherein.

DETAILED DESCRIPTION OF THE INVENTION

The present invention provides a method and system for the ultrasonic diagnosis and lysis of coronary artery thromboses.

The principles and operation of the method and system of the present invention may be better understood with reference to the drawings and the accompanying description.

It will be well known to one familiar with the art that ultrasound signals transmitted into organic tissue at a given frequency (known as the "first harmonic") are reflected off of a reflector in the organic medium as an ultrasound signal comprised of multiple frequency components. The central frequency component of the signal will be equal to the first harmonic, while additional components of the reflected signal will have frequencies equal to half of, and to twice and possibly three times that of the first harmonic (termed the "half", the "second" and "third" harmonics, respectively). This phenomenon of multiple harmonics in a reflected ultrasound signal occurs due to the non-linearity of organic tissue as an ultrasound conductive/reflective medium It is further known that the second harmonic component of ultrasound signals reflected off of an ultrasound contrast agent (such as MRX-408, ImaRx Pharmaceutical Corp., Tucson, Ariz.) is relatively greater than the second harmonic components of ultrasound signals reflected off of an organic tissue reflector (such as muscle blood vessels or thrombus). Thus, an ultrasound signal reflected off of an ultrasound contrast agent has a higher ratio of second harmonic to fast harmonic frequency components than does a signal reflected off of an organic reflector. The "second to first harmonic ratio" in a reflected ultrasound signal is thus dependent on the nature of the reflecting object (be it a contrast agent or organic tissue), rather than on the amplitude of the reflected waves. Thus even a small quantity of ultrasonic contrast agent (generating reflected ultrasound signals of low amplitude) located within a highly echogenic organic tissue (generating multiple reflected ultrasound signals of high amplitude), can be ultrasonically identified by analyzing the second to first harmonic ratio of the received signals, even though the contrast agent itself cannot be discerned by standard ultrasonic imaging techniques (which construct a two-dimensional image based on the amplitudes of the received echo signals). If a thrombus-specific ultrasound contrast agent (which adheres specifically to intravascular thrombi) is injected intravenously, and thereafter ultrasonic interrogation of the subject's heart reveals a high second to first harmonic ratio in received ultrasonic signals, the presence of contrast agent in the heart (indicating the existence of a coronary artery, or other intracardiac, thrombosis) can be presumed.

Figure 1:
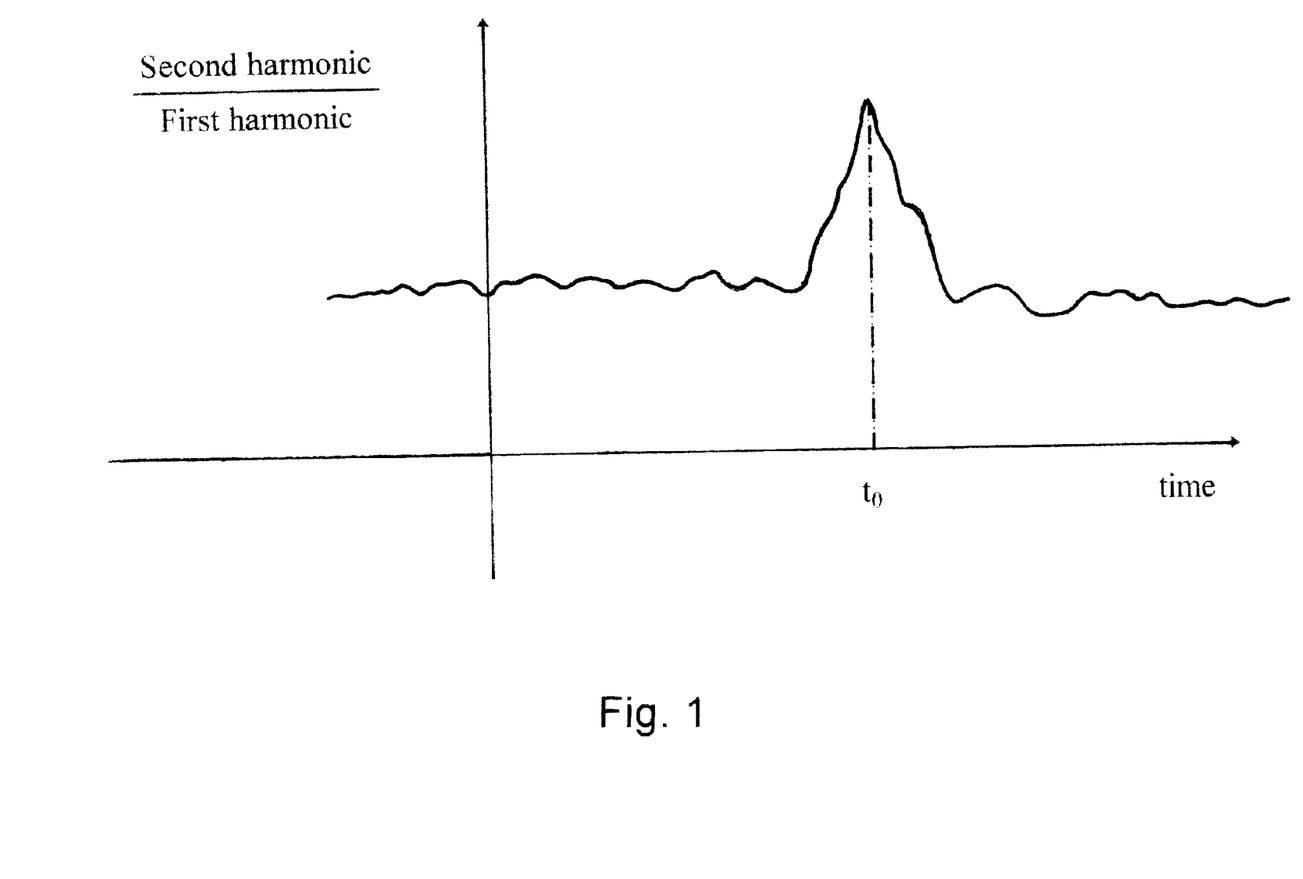
FIG. 1 is a graph of ratio of second harmonic to first harmonic components of a received ultrasound signal as a function of elapsed time.

Turning now to FIG. 1, the result of ultrasonic interrogation of the heart of a patient (who was suspected of having a coronary artery thrombosis) is shown, after injection of Optison (a non-specific contrast agent mimicking the mechanical properties of MRX-408) had been performed.

The ultrasound signals were transmitted at a frequency of 1.5 MHz and reflected signals were received by two crystals, one tuned to 1.5 MHz (being the first harmonic of the transmitted signal), and the second tuned to 3 MHz (being the second harmonic of the transmitted signal). The graph plots the ratio of second harmonic to first harmonic components of each received ultrasound signal as a function of the time elapsed since transmission of the signal. An increase in the second to first harmonic ratio can be seen at time to, indicating the presence of MRX408 (most likely due to a coronary artery thrombosis) within the field of ultrasonic interrogation As to (the time-of-flight for the signal with a high second to first harmonic ratio) is dependent on the distance between the contrast agent (e.g. MRX408) reflector and the ultrasound receiver, additional receivers located at different locations on the patient's chest will each exhibit different values for to. If the geometric relationship between the three (or more) receivers on the patient's chest is known, an analysis of three such values for to allows the three-dimensional spatial location of the MRX408 reflector, in relation to the ultrasound receivers, to be calculated by triangulation.

The values of $t_0$ for each of multiple transceivers receiving echoes from a single reflective source can be used to generate a firing sequence for pulsed ultrasound signals transmitted from each of the multiple transceivers with such timing as to achieve maximal summation of the ultrasound energy at the site of the reflective source (namely, the MRX-408 contrast agent on a coronary thrombosis). If the power of the transmitted pulses is adequate, sufficient ultrasound energy can be focused on the thrombus to induce sonoparation and clot lysis, without damaging surrounding tissue.

Figure 2:
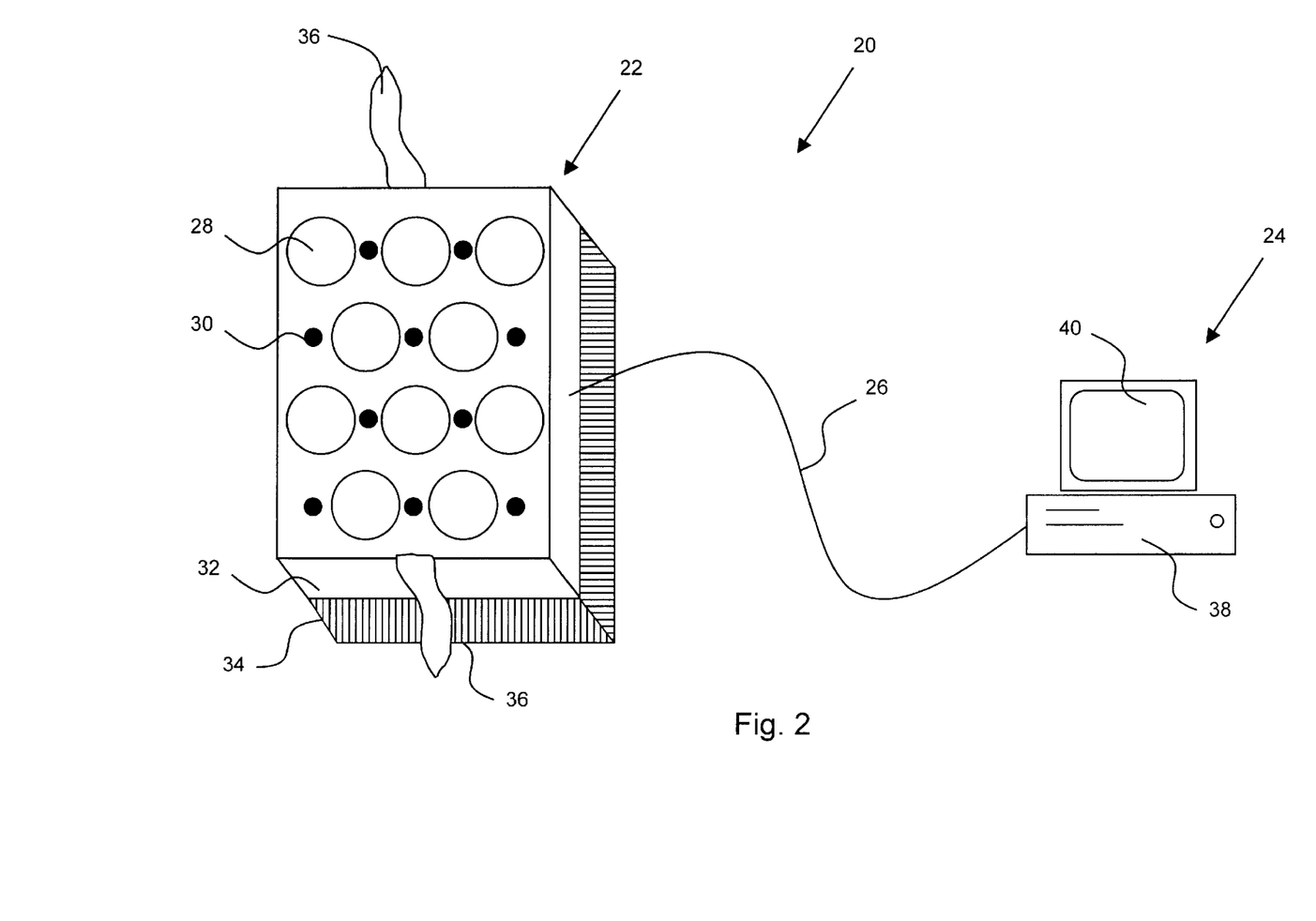
FIG. 2 is a diagram of the principle components of a device capable of achieving ultrasonic coronary artery thrombolysis in terms of the present invention.

FIG. 2 is a diagram of the principle components of an ultrasonic thrombosis detection and lysis apparatus, hereinafter referred to as device 20, capable of achieving ultrasonic coronary artery thrombolysis based on the principles outlined in FIG. 1 above. As shown in the figure, device 20 is composed of a transducer pad 22, a control unit 24, and a cable 26 connecting transducer pad 22 and control unit 24. In an alternative embodiment (not shown in FIG. 2), control unit 24 is mounted directly onto transducer pad 22. Transducer pad 22 contains multiple ultrasound transducer crystals 28 and multiple ultrasound receiving crystals 30, in a preferred embodiment of the present invention, transducer pad 22 includes sixty-four of transducer crystals 28 and sixty-four of receiving crystals 30. In an alternative embodiment, transducer pad 22 includes sixty-four of transducer crystals 28 and one hundred and twenty eight of receiving crystals 30. Transducer crystals 28 and receiving crystals 30 are embedded within a supporting sheet 32. Sheet 32 is a sheet of rigid material, typically plastic, which does not allow movement or translation between crystals 28 and 30 embedded within sheet 32. Crystals 28 and 30 are arranged in a checkerboard fashion relative to each other in sheet 32, or in any other arrangement within sheet 32 provided that the relative locations, of each crystals 28 and 30 to each other are fixed and known. Each of transducer crystals 28 and 30 are connected to cable 26. One surface of sheet 32 is affixed to a layer 34 of ultrasound coupling medium. Layer 34 is engineered as a plastic cushion enclosing aqueous ultrasonic coupling gel, and is sufficiently flexible as to conform to the contours of the chest. Crystals 28 and 30 are oriented in sheet 32 such that the transmitting/receiving surface of each of crystals 28 and 30 faces layer 34. Layer 34 serves as an interface between crystals 28 and 30 on the one hand, and the body of the patient, on the other.

A strap 36 is affixed to either end of sheet 32. Sheet 32 can be held in place on the patient's body by straps 36. Several units of transducer pad 22 may be connected to each other in series (not shown) for use on a patient with a larger chest wall. Each of crystals 28 and 30 are connected to a computer processor 38 in control unit 24, by means of cable 26. Control unit 24 further includes a display 40. In alternative embodiments, sheet 32 can be held in place on the patient's body by the operator of device 20, or by other means.

Figure 3:
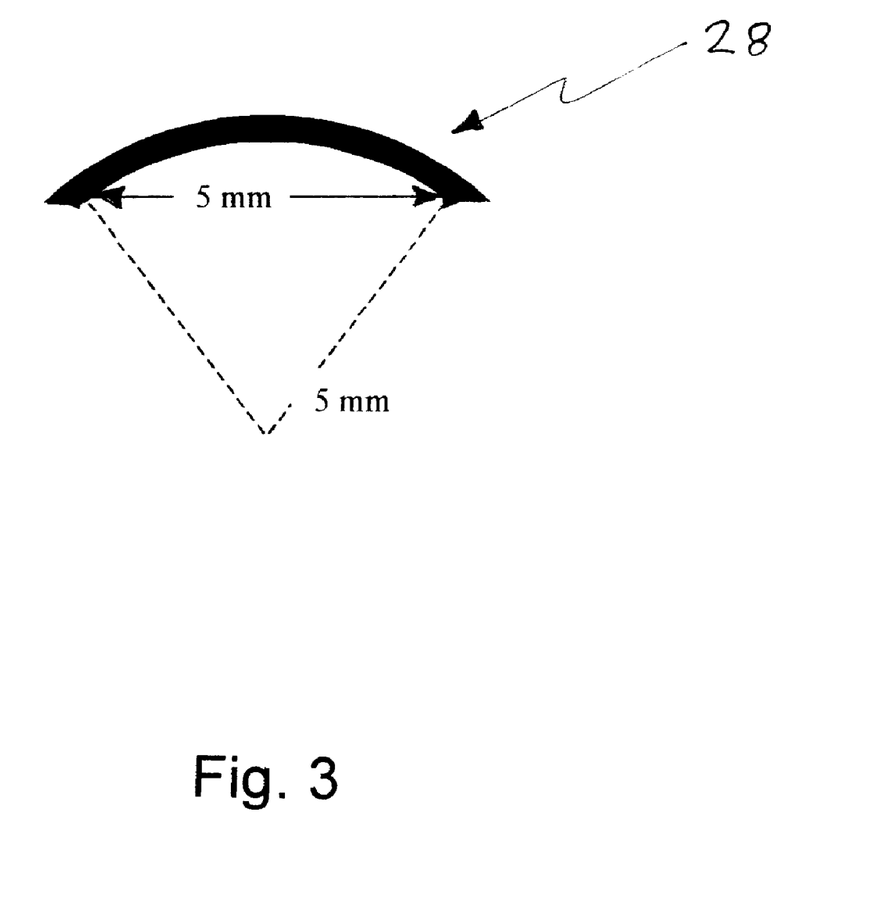
FIG. 3 is a diagram of the geometry of a transducer crystal.

FIG. 3 is a diagram of the geometry of each of transducer crystals 28. Each crystal 28 is convex in shape, typically with a 5 mm. radius of curvature, operative to produce an omnidirectional ultrasound beam when activated. Transducer crystals 28 are typically tuned to transmit at 1.5 MHz. with receiving crystals 30 typically divided into three groups, a third being tuned to receive ultrasound signals at 1.5 MHz, a third of receiving crystals 30 being tuned to receive ultrasound signals at 3.0 MHz, and a third of receiving crystals 30 typically being tuned to receive ultrasound signals at 0.75 MHz. In an alternative preferred embodiment, not shown in FIG. 3, crystal 28 is a flat element (which transmits a beam whose divergence is limited by the ratio of the transducer size to the wavelength used) capable of transmitting at 1.5 to 3 MHz, and ranging in size between 1 and 3 mm. In this embodiment, a two dimensional array of flat elements of such size as to generate an effect of a convex (diverging beam) virtual source during the "diagnostic" phase of functioning of device 20, and a concave (converging beam) during the "therapeutic" phase of functioning of device 20, is used (see explanation below describing the "diagnostic" and "therapeutic" phases of functioning of the present invention). The specifications of crystals 28 are standard specifications well known to one familiar with the art.

In the preferred embodiment, device 20 functions as described below. The operator of device 20 places pad 22 (typically one to five such pads, depending on the size and shape of the patient's thorax, held together by strap 36 or by the operator) on the chest of a patient in whom a coronary thrombosis is suspected, such that layer 34 is on the skin surface and that the patients heart is covered by pad 22. A thrombus-specific ultrasound contrast agent (M-408) is injected intravenously into the patient by the operator. The operator then initiates operation of device 20 by means of control unit 24. Device 20 first performs a process of thrombus detection (the diagnostic phase). In this process, one of transducer crystals 28 transmits a pulsed ultrasound signal typically with a central frequency of 1.5 MHz into the chest of the patient. Reflected ultrasound signals are received by all of receiving crystals 30, some of which are tuned to the first harmonic (1.5 MHz) some of which are tuned to the second harmonic (3 MHz), and others of which are tuned to the half harmonic (0.75 MHz). The received signals are quantified and the ratio of second to first harmonic components, or the ratio of the half to first harmonic components, in the received signals, are calculated by computer processor 38. A second transducer crystal 28 then transmits a pulsed ultrasound signal in the same manner as had the first transducer crystal 28, with reflections from this signal being received by receiving crystals 30 as described above. This process is repeated sequentially for all of transducer crystals 28. If none of receiving crystals 30 receive a reflected signal having a significantly high second to first harmonic, as calculated by computer processor 38, an output on monitor 40 indicates to the operator of device 20 that no thrombosis was detected. A good signal is defined as a signal for which the ratio of second to first harmonics is in the range of 3:1 to 10:1, and preferably between 5:1 and 7:1. If any of receiving crystals 30 receive a reflected signal having a significantly high second to first harmonic ratio, as calculated by computer processor 38, an output on monitor 40 indicates to the operator of device 20 that a thrombosis has been detected. In this event, the operator administers an intravenous thrombolytic agent (such as tPA) and then manually initiates a process (typically by pressing a button) of clot localization and immediate lysis by device 20. In an alternative embodiment, the intravenous thrombolytic agent may be bound to a thrombus-specific ultrasound contrast agent.

The initial step in the process of clot localization and lysis (the therapeutic phase) is the same as the process of thrombus detection (the diagnostic phase) described above. Once all of transducer crystals 28 have transmitted a pulsed ultrasound signal, computer processor 38 calculates which of transducer crystals 28 generated the reflected signal having the highest second to first harmonic ratio, and designates this transducer as the reference transducer for time-of-flight calculations. In addition whichever of receiving crystals 30 received a reflected signal over a predefined threshold amplitude are designated as being receivers unobstructed by the patient's ribs, and appropriate for utilization by device 20 in the process of thrombolysis. All other receivers are designated as being obscured by the patient's ribs, and are not utilized firer by device 20. Computer processor 38 then calculates the time-of-flight ($t_0$) for each reflected ultrasound signal having a significant second to first harmonic ratio received by receiving crystals 30 (as demonstrated in FIG. 1 above). These time durations (less a preset constant which biases for the time-of-flight from transducer crystal 28 to the thrombus) are then used by computer processor 38 to calculate the spatial location of the diagnosed coronary thrombosis, and a timing sequence by which transducer crystals 28 may transmit a pulsed ultrasound signal so as to achieve thrombolysis. This turning sequence is such that omnidirectional ultrasound waves transmitted by transducer crystals 28 will summate at the calculated location of the coronary thrombosis, so as to achieve a focused field intensity of up to 190 W/cm$^2$, or a maximum negative pressure of 2.3 MPa, and induce thrombolysis. This pulsed ultrasound signal is typically a single pulse of 1–3 cycles (preferably 2 cycles). The repetition rate is dependent upon the range to the clot, as once a pulse has been fired, a second pulse cannot be fired until all echoes from the first pulse have subsided. Typical times between pulses are 100 and 300 microseconds (repetition frequencies between 3 and 10 KHz). Computer processor 38 then activates transducer crystals 28 according to the calculated timing sequence. Immediately after performing a "therapeutic" ultrasound transmission, system 20 repeats a "diagnostic" phase so as to detect if thrombus is still present, and if so, a repeat therapeutic cycle is performed. Several such cycles are performed until device 20 no longer detects evidence of thrombus. When this happens, monitor 40 indicates to the operator that thrombolysis has been performed. The process of thrombus identification and thrombolysis is achieved within several microseconds. The operator may then repeat the process of thrombosis detection and lysis by device 20 again, as needed.

In a second preferred embodiment of the present invention, during the thrombus identification process, transducer crystals 28 transmit pulsed ultrasound signals, as described above for the first preferred embodiment, and the reflected signals are received not only by receiving crystals 30, but also by some of transducer crystals 28, which switch from transmitter electronic functioning to receiver electronic functioning, tuned to the first harmonic.

Figure 4:
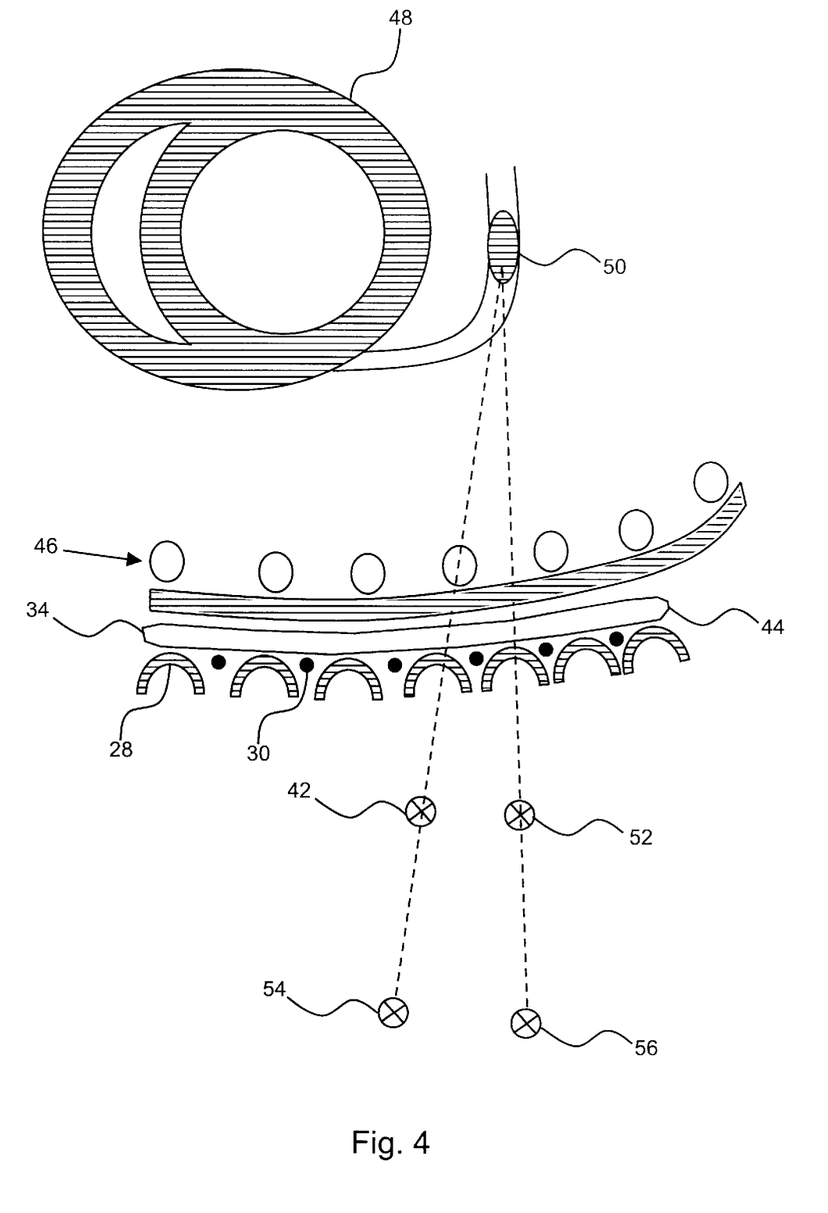
FIG. 4 is a diagram of transducer crystals in relation to the chest wall.

FIG. 4 demonstrates a third preferred embodiment of the present invention. In this embodiment, crystals 28 are flat elements. In the figure transducer crystals 28 and receiving crystals 30 are shown in position on the skin surface 44 of a patient's chest wall. Underlying skin surface 44 are ribs 46, the heart 48, and a coronary artery thrombosis 50. In this embodiment, during the thrombus identification process transducer crystals 28 all transmit ultrasound pulses as a "phased array" (i.e. in a synchronously staggered manner), such that summation of all the transmitted signals results in a convex (diverging) omnidirectional signal having as its apparent origin a "virtual source" located at a virtual point 42 outside of the patients body. By changing the relative timing at which each of transducer crystals 28 transmit, the location of the virtual source can be moved. Ultrasound signal intensity at the site of thrombus 50 will depend on the position of virtual point 42, due to obstruction by ribs 46 of the signals transmitted by transducer crystals 28. Thus, for example moving the virtual source from virtual point 42 to virtual point 52 in FIG. 4 will significantly enhance the signals reflected from thrombus 50. Since the ultrasound pressure amplitude at any point is dependant on the distance between that point and the source of the ultrasound signal (be it "real" or "virtual"), shifting the ultrasound source further away from skin surface 44 (e.g. from virtual point 42 to virtual point 54, or from virtual point 52 to virtual point 56) will result in lower ultrasonic intensities at skin surface 44 (for a given field intensity at the site of thrombus 50).

In terms of the third preferred embodiment of the present invention, ultrasound signals are transmitted by traducer crystals 28 from a virtual source, and reflected echoes are received by receiving crystals 30. The location of the virtual source is then changed by computer processor 38, in accordance with a preprogrammed set of virtual locations relative to sheet 32 stored in computer processor 38, and the process is repeated, until such time as a signal with a maximal second to first harmonic ratio is received by receiving crystals 30. The search for the signal having a maximal second to first harmonic ratio is initiated during an initial clot detection phase, when a very large area is scanned looking for the virtual location associated with a maximal echo. Once this position has been identified, the search is renewed after each thrombolysis sequence (lasting about 0.1 seconds) in a limited area, so as to compensate for minor changes in the position of sheet 32 (relative to the rib cage). Patient respiration or instability of the operator's hand holding sheet 32 could cause such changes in position The process of thrombolysis in the second and third embodiments of the present invention is identical to that in the first embodiment, as described above. The checkerboard arrangement of transducer crystals 28 and receiving crystals 30 relative to each other means that each one of transducer crystals 28 is surrounded by several of receiving crystals 30, in a spatially fixed manner. The differences in time-of-flight for the same received signal by each of "surrounding" receiving crystals 30 allows computer processor 38 to calculate the distance between each "central" transducer crystal 28 and the thrombus, and therefore the proper firing timings for all of transducer crystals 28. In order to improve measurement of the second harmonic frequency by receiving crystals 30, the pulses transmitted by transducer transmitting crystals 28 may be multiplied in time by a 'window' (e.g. a Gaussian function) so as to minimize second harmonics of the transmitted frequency, in a manner known as apodization. An alternative or additional method for improving the measurement of the second harmonic frequency by receiving, crystals 30 is to transmit the pulses transmitted by transducer transmitting crystals 28 according to the technique of "pulse inversion harmonics". In this technique, an ultrasound pulse is transmitted and the returned fundamental signal as well as its harmonic components are digitally stored. Immediately thereafter, a pulse that is the inversion of the original pulse is transmitted, and the returned inverse fundamental signal as well as its harmonic components are digitally stored. Summation of the returned signals is then performed, resulting in elimination of the fundamental signals, and reinforcement of the harmonic components.

In order to improve the signal-to-noise ratio, a coded excitation scheme (a Gollay code) may be used. In such a case, transducer crystals 28 transmit a randomly spaced train of pulses with alternating signs. When receiving crystals 30 receive the echoes, the signals are delayed and summed (or subtracted) in accordance with the appropriate "key" (a predetermined sequence of pulses, with well defined spacing between pulses as well as pulse polarities selected) so as to generate high signal-to-noise outputs proportional to the first (or second) harmonic components.

In a further embodiment of the present invention a standard two-lead ECG machine (not shown) with an automatic R-wave detector may be incorporated into device 20. In this embodiment, computer processor 38 samples the output of the R-wave detector, and the functioning of device 20 is synchronized with the cardiac cycle such that ultrasonic thrombolysis occurs only during diastole.

Figure 5:
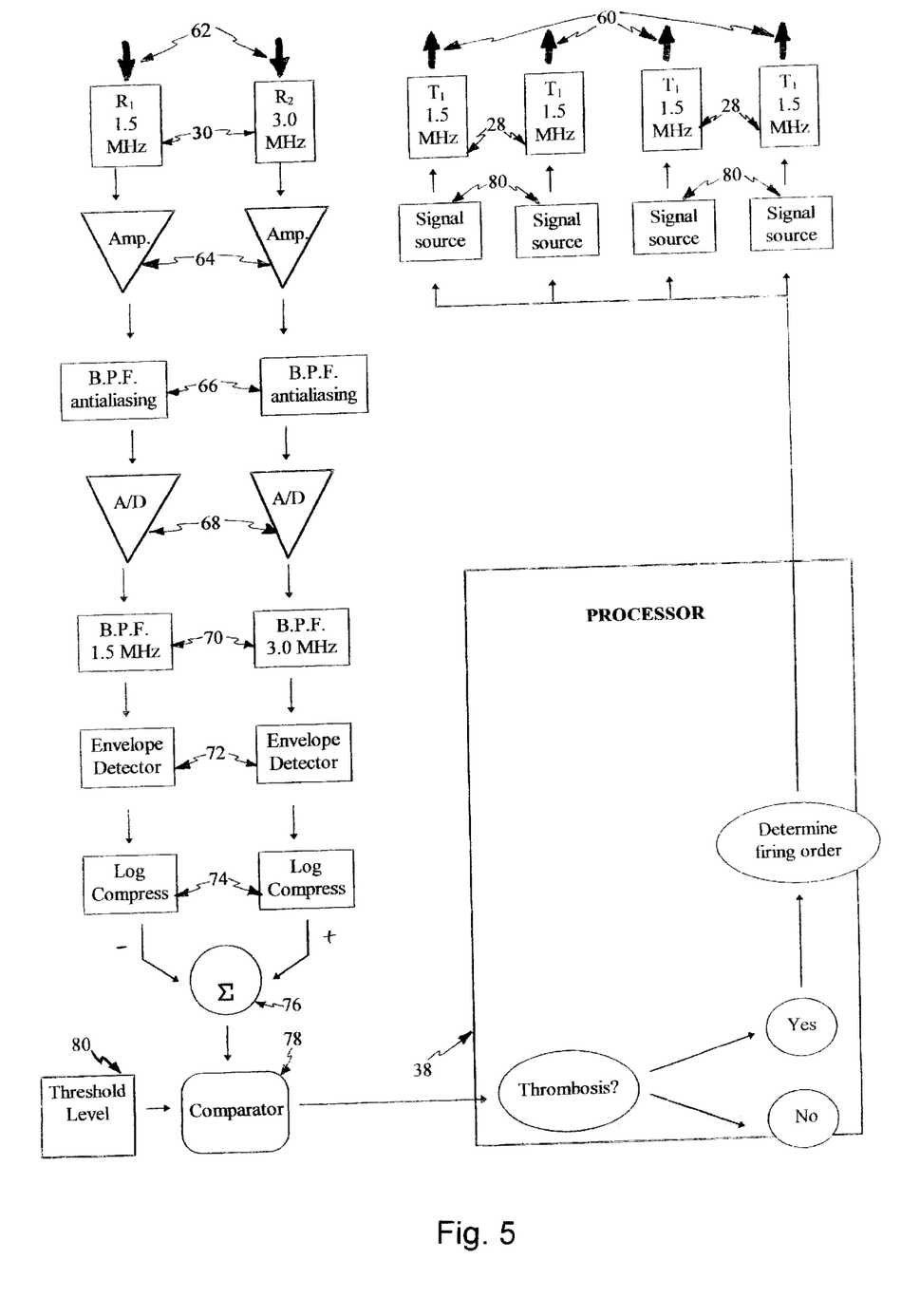
FIG. 5 is a block diagram detailing the process of ultrasonic thrombosis diagnosis and thrombolysis.

FIG. 5 is a block diagram detailing the process of ultrasonic thrombosis diagnosis, and thrombolysis, as embodied in the present invention The diagram describes a set of four transmitters 28 tuned to 1.5 Mkz and two receivers 30 (one tuned to 1.5 MHz and the other tuned to the second harmonic, 3 MHZ) For purposes of illustration, only four of transducer crystals 28 and two of receiver crystals 30 are shown, although it should be understood that multiple units of crystals 28 and 30 function simultaneously as described in FIG. 5. Receivers 30 receive a reflected ultrasound signal 62 which had been transmitted 60 at a central frequency of 1.5 MHz by one of transmitters 28. Received signals 62 are then amplified 64 and undergo BPF (Band Pass Filter) antialiasing 66 and analog-to-digital conversion 68. The digital signals then pass through Band Pass Filters 70 tuned to either the first or second harmonic of transmitted signal 60. Band Pass Filters 70 select the frequency components of the signals equal to the relevant harmonic. The output signals from BPF 70 are input to envelope detectors 72 which detect and quantify the amplitude of the harmonic signals selected by BPF's 70. The quantified signals then undergo log compression 74, and the output log quantities are algebraically summated 76, with one quantity assigned a positive sign and the other quantity a negative sign, so as to generate a logarithm of the ratio of the two measured harmonics of signals 62. This value is input to a comparator 78, which compares the measured value with a threshold level 80 designated by the operator. When the measured value exceeds the threshold level a diagnosis of thrombosis is determined by processor 38. When processor 38 determines a diagnosis of thrombosis, processor 38 then determines which of transducer crystals 28 have acoustic access to the diagnosed thrombus. In the event that crystal 28 functions as a transceiver (switching from receiver electronic functioning to transmitter electronic functioning), this determination is made in the event that signal 62 had been received by crystal 28. Alternatively, in the event that crystal 28 functions as a transmitter only, this determination is made in the event that signal 62 had been received by those of receiving crystals 30 in the immediate vicinity of crystal 28, wherein the spatial relationship between crystals 28 and 30 in sheet 32 are fixed and known. Processor 38 then calculates an appropriate firing order for transducer crystals 28, based on the measured times-of-flight of signals 62 and the geometric relationships between crystals 28 in sheet 32, so as to focus the transmitted ultrasound energy on the diagnosed thrombus. Processor 38 then initiates functioning of signal source 80, which is a pulse generator functional to initiate ultrasound transmission by transducer crystals 28 in a "phased array mode". Processor 38 then repeats the cycle of thrombosis diagnosis and thrombolysis according to a prescribed number of cycles, or until a thrombus is not diagnosed.

Figure 6:
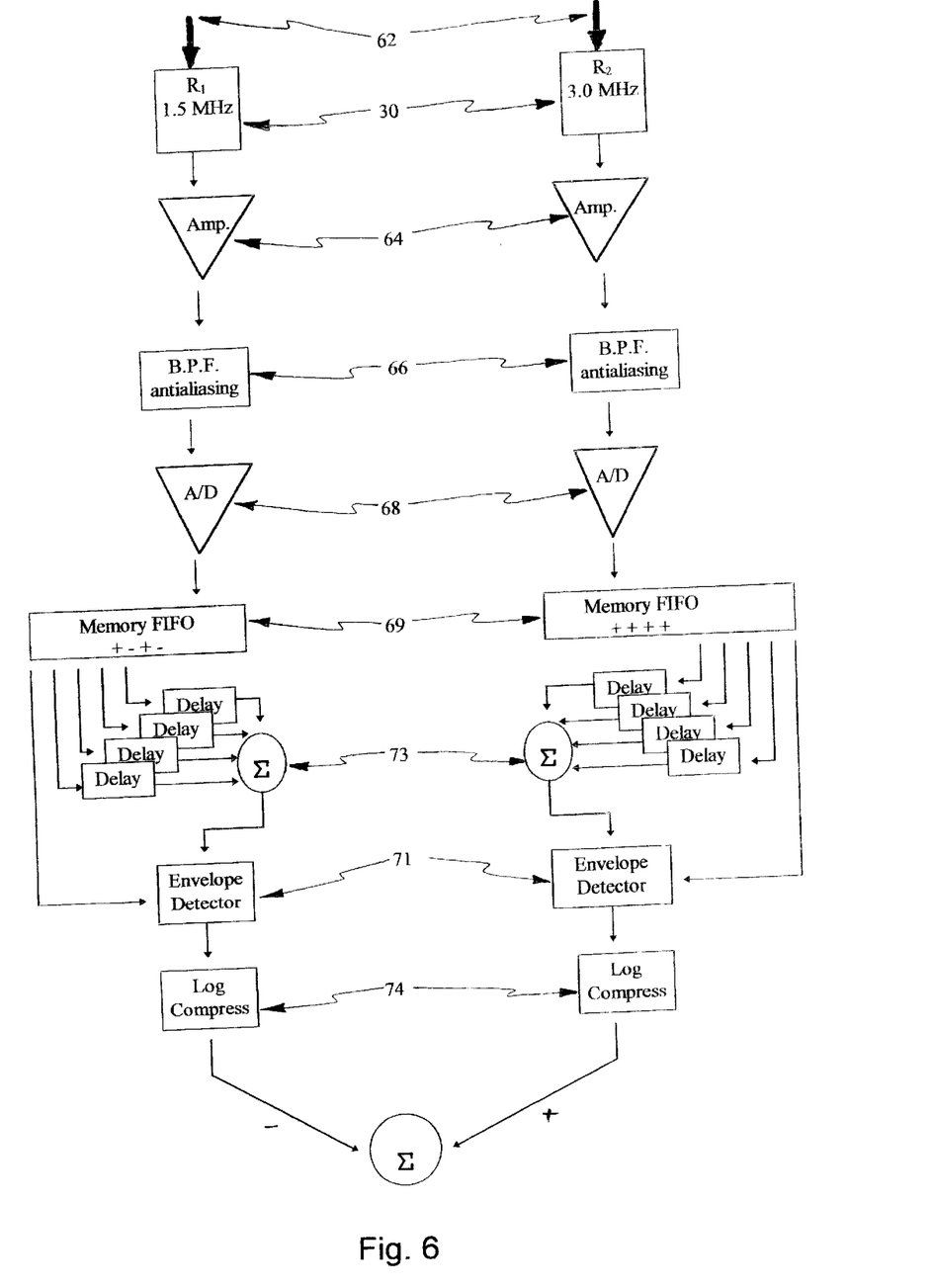
FIG. 6 is a block diagram detailing the process of ultrasonic thrombosis diagnosis utilizing a coded excitation (Gollay) transmission scheme.
Figure 7:
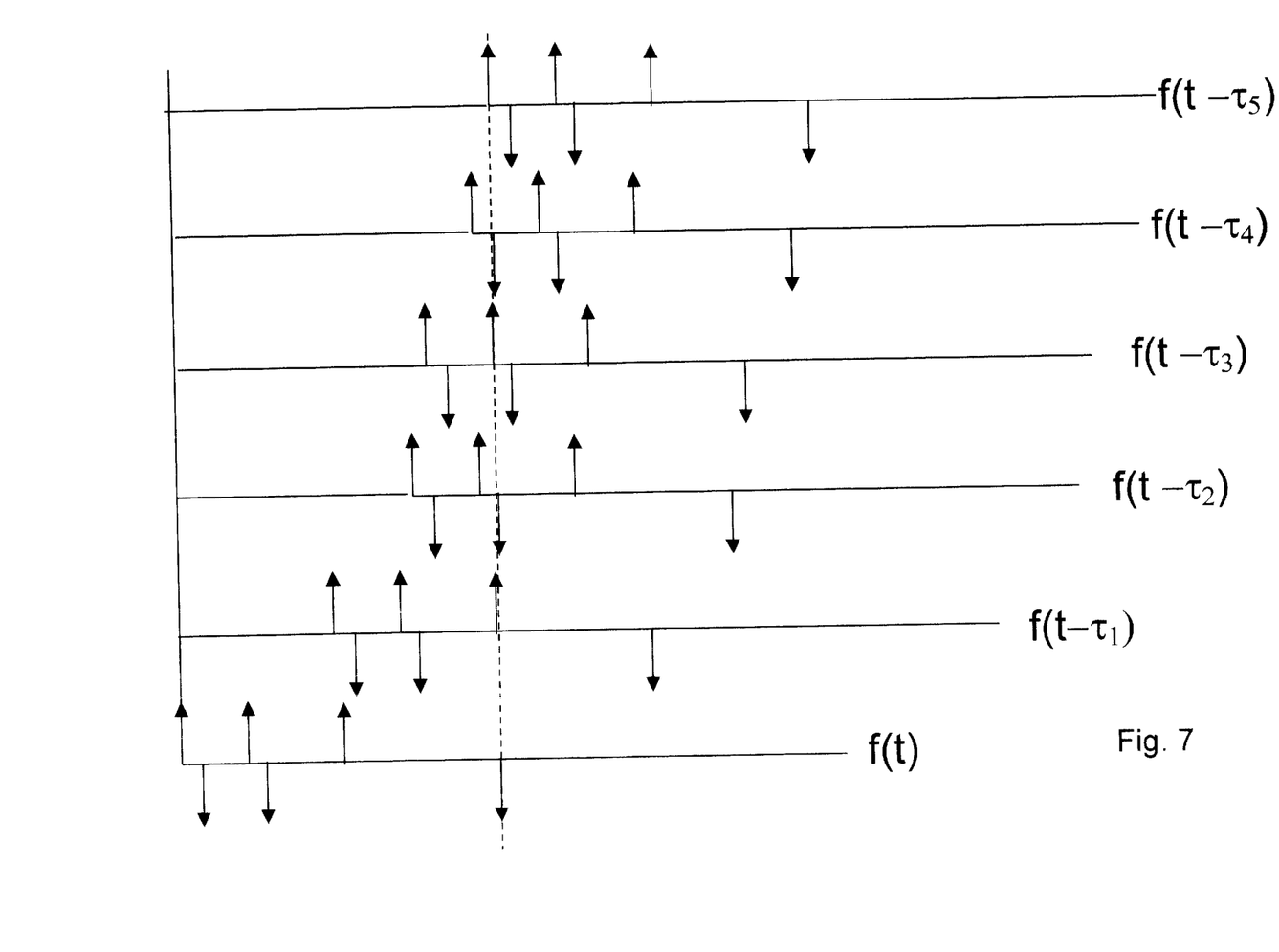
FIG. 7 is a graphic representation of a Gollay transmission sequence.

FIG. 6 is a block diagram detailing the process of ultrasonic thrombosis diagnosis utilizing a coded excitation (Gollay) transmission scheme, as embodied in the present invention. Elements 30 through 68 of FIG. 6 are essentially identical to those of FIG. 5 and perform identical functions. Elements 69 and 73 can be understood by referring to FIG. 7, which is a graphic representation of a Gollay transmission sequence. The pulse sequence transmitted and received is f(1). The second harmonic component is derived by summing the properly delayed exemplars of ft), $$F(t) = \sum_{i=1}^{N} f(t - \tau_i)$$

namely:
and then applying a high-pass filter to F(t) to remove all first harmonic components.

The first harmonic component is derived by first generating:

$$G(t) = \sum_{i=1}^{N} (-1)^i f(t - \tau_i)$$

and then applying a low-pass filter to remove harmonics higher than the first.

The output harmonic components are then input to envelope detectors 71 which detect and quantify their amplitudes. The quantified signals then undergo log compression 74, and the output log quantities are algebraically summated and processed further as described in FIG. 5 above.

Although the present invention has been described with reference to the second harmonic of the transmitted ultrasonic signal, it should be understood that any other harmonic of the transmitted signal, for example the half harmonic, the third harmonic or the fourth harmonic (or indeed any harmonic which is different from the central frequency of transmission, the first harmonic), may be used instead of the second harmonic, or in addition to the second harmonic, without departing from the spirit of the present invention. Furthermore, although the present invention has been described with reference to frequency characteristics of the received ultrasonic signal it should be understood that temporal characteristics of the received signal other than "frequency" (for example, characteristics generated by performing wavelet analysis or decomposition on the received ultrasound signal rather than Fourier analysis) may be analyzed in a similar manner to that described above for frequency characteristics, so as to rapidly diagnose a coronary thrombosis, without departing from the spirit of the present invention. By "temporal characteristic" is meant any ultrasound characteristic or parameter that is a function of time, and requires, of necessity, a time axis for its graphic depiction "Temporal characteristics" are thus to be contrasted with those ultrasound characteristics or parameters which can be quantified in terms independent of time, for example amplitude and power.

There has thus been described a method for achieving rapid ultrasonic coronary thrombolysis. In contrast to other ultrasonic thrombus detection methods, the method of the present invention does not require or perform two-dimensional imaging of the thrombus, but rather analyzes harmonic characteristics of received signals to automatically calculate if a thrombus is present or not. The method is thus very rapid. Furthermore, the ability to calculate the exact spatial location of the thrombus in real time allows for the focusing of ultrasound energy only on the thrombus, and not on surrounding tissues, making the method safe.

It is appreciated that one or more of the steps of any of the methods described herein may be omitted or carried out in a different order than that shown, without departing from the true spirit and scope, of the invention.

While the present invention as disclosed herein may or may not have been described with reference to specific hardware or software, the present invention has been described in a manner sufficient to enable persons of ordinary skill in the art to readily adapt commercially available hardware and software as may be needed to reduce any of the embodiments of the present invention to practice without undue experimentation and using conventional techniques.

While the present invention has been described with reference to one or more specific embodiments, the description is intended to be illustrative of the invention as a whole and is not to be consumed as limiting the invention to the embodiments shown It is appreciated that various modifications may occur to those skilled in the art that, while not specifically shown herein, are nevertheless within the true spirit and scope of the invention.

What is claimed is:

1. A method for lysing a thrombus in a human body, comprising
   a) introducing an ultrasound contrast agent into the human body;
   b) transmitting an ultrasound signal towards the thrombus at at least one transmission frequency;
   c) receiving an ultrasound signal reflected off of said thrombus said received ultrasound signal having a temporal characteristic;
   d) calculating a spatial location of said thrombus from said temporal characteristic; and
   e) transmitting ultrasound energy towards said spatial location.

2. The method of claim 1, wherein said transmitted ultrasound signal is transmitted as a Gollay code.

3. The method of claim 1, wherein said transmitted ultrasound signal is apodized.

4. The method of claim 1, wherein said transmitted ultrasound signal includes two ultrasound pulses of inverse phase to each other.

5. The method of claim 1, wherein said transmitted ultrasound signal is transmitted from a plurality of ultrasound transmitters generating an apparent single virtual source for said transmitted ultrasound signal.

6. The method of claim 1, wherein said temporal characteristic is a frequency characteristic.

7. The method of claim 6, wherein said frequency characteristic is an increased ratio of a frequency component equal to a second harmonic of said transmission frequency to a frequency component equal to a first harmonic of said transmission frequency.

8. The method of claim 6, wherein said frequency characteristic is an increased ratio of a frequency component equal to a half harmonic of said transmission frequency to a frequency component equal to a first harmonic of said transmission frequency.

9. The method of claim 1, wherein said calculation of said spatial location is effected utilizing time-of-flight data.

10. The method of claim 1, wherein said transmitted ultrasound energy is transmitted from a plurality of ultrasound transmitters generating an apparent single virtual source for said transmitted ultrasound energy.

11. The method of claim 10, wherein said plurality of ultrasound transmitters are located on a chest wall of the human body.

12. The method of claim 1, wherein said transmitting of said ultrasound energy is achieved during cardiac diastole.

13. An apparatus for treating a thrombus in a human body, comprising
    a) a sheet of material, said sheet being placeable on the human body;
    b) a plurality of ultrasound transmitters for transmitting ultrasound signals into the human body, said transmitters being fixedly located within said sheet, and said transmitters being oriented within said sheet such that said transmission is effected into the human body;
    c) a plurality of ultrasound receivers for receiving ultrasound signals reflected from the human body, said receivers being fixedly located within said sheet, and said receivers being oriented within said sheet such that said reception is effected from the human body;
    d) a layer of ultrasound coupling medium applied to a surface of said ultrasound transmitters and said ultrasound receivers, said layer being conformable to a contour of the human body; and
    e) a processor for processing said received signals, said processor being functional to
       i) calculate a temporal characteristic of said received signals, and
       ii) diagnose a thrombus from said calculated temporal characteristic.

14. The apparatus of claim 13, wherein said processor is further functional to:
    iii) quantify a time-of-flight for said received signals, and
    iv) calculate a spatial location of said thrombus from said time-of-flight quantities.

15. The apparatus of claim 14, wherein said processor is further functional to:
    v) calculate a pattern of transmission for said ultrasound transmitters such that transmitted ultrasound energy is focused on said calculated spatial location, and
    vi) effect transmission of said ultrasound transmitters according to said calculated pattern.

16. The apparatus of claim 13, wherein said sheet includes plastic.

17. The apparatus of claim 13, wherein said transmitters and said receivers are arranged in a checkerboard pattern relative to each other in said sheet.

18. The apparatus of claim 13, wherein said calculated temporal characteristic is an increased ratio of a frequency component equal to a second harmonic of said transmission frequency to a frequency component equal to a first harmonic of said transmission frequency.

19. The apparatus of claim 13, wherein said calculated temporal characteristic is an increased ratio of a frequency component equal to a half harmonic of said transmission frequency to a frequency component equal to a first harmonic of said transmission frequency.

* * * * *